United States Patent [19]

Hodosh et al.

[11] 4,410,323
[45] Oct. 18, 1983

[54] PREDOSED DISPOSABLE SYRINGE

[76] Inventors: Milton Hodosh, 72 Overhill Rd., Providence, R.I. 02906; Milton H. Lipsky, Pine Tree La., West Greenwich, R.I. 02816

[21] Appl. No.: 374,333

[22] Filed: May 3, 1982

Related U.S. Application Data

[63] Continuation of Ser. No. 162,134, Jun. 23, 1980, abandoned, which is a continuation-in-part of Ser. No. 912,386, Jun. 5, 1978, abandoned, and a continuation-in-part of Ser. No. 931,209, Aug. 4, 1978, abandoned.

[51] Int. Cl.³ .............................................. A61M 1/00
[52] U.S. Cl. ................................................... 604/212
[58] Field of Search ................. 604/212, 216, 192, 28, 604/187, 200–204, 82–91, 48

[56] References Cited

U.S. PATENT DOCUMENTS 2,688,963  9/1954  Smith ................................. 604/212
3,938,514  2/1976  Boucher ............................. 604/216

FOREIGN PATENT DOCUMENTS 826918  8/1968  Canada ................................. 604/212
286616  8/1915  Fed. Rep. of Germany ...... 604/212
428093  7/1969  Switzerland ........................ 604/212
424599  2/1935  United Kingdom ................ 604/212

*Primary Examiner*—John D. Yasko
*Attorney, Agent, or Firm*—Salter & Michaelson

[57] ABSTRACT

A disposable syringe for use in administering a medication including a flexible, compressible container, means located on said container for mounting a needle thereon, and a holder for said container that defines a means for compressing the container to eject the medication through said needle, said holder being defined by a flat flexible member having a central opening for receiving said container therein, and securing means associated with said holder for locating said container therein so that compression of said holder results in the compressing of said container to cause the medication to be ejected through said needle. In another form of the invention, a diluent contained in either a pod or container is mixed with a powdered medicated material in the container to form a preselected medicated fluid therein, the pod being removable from the container for thereafter mounting the needle thereon for the dispensing of the medicated fluid therethrough.

13 Claims, 12 Drawing Figures

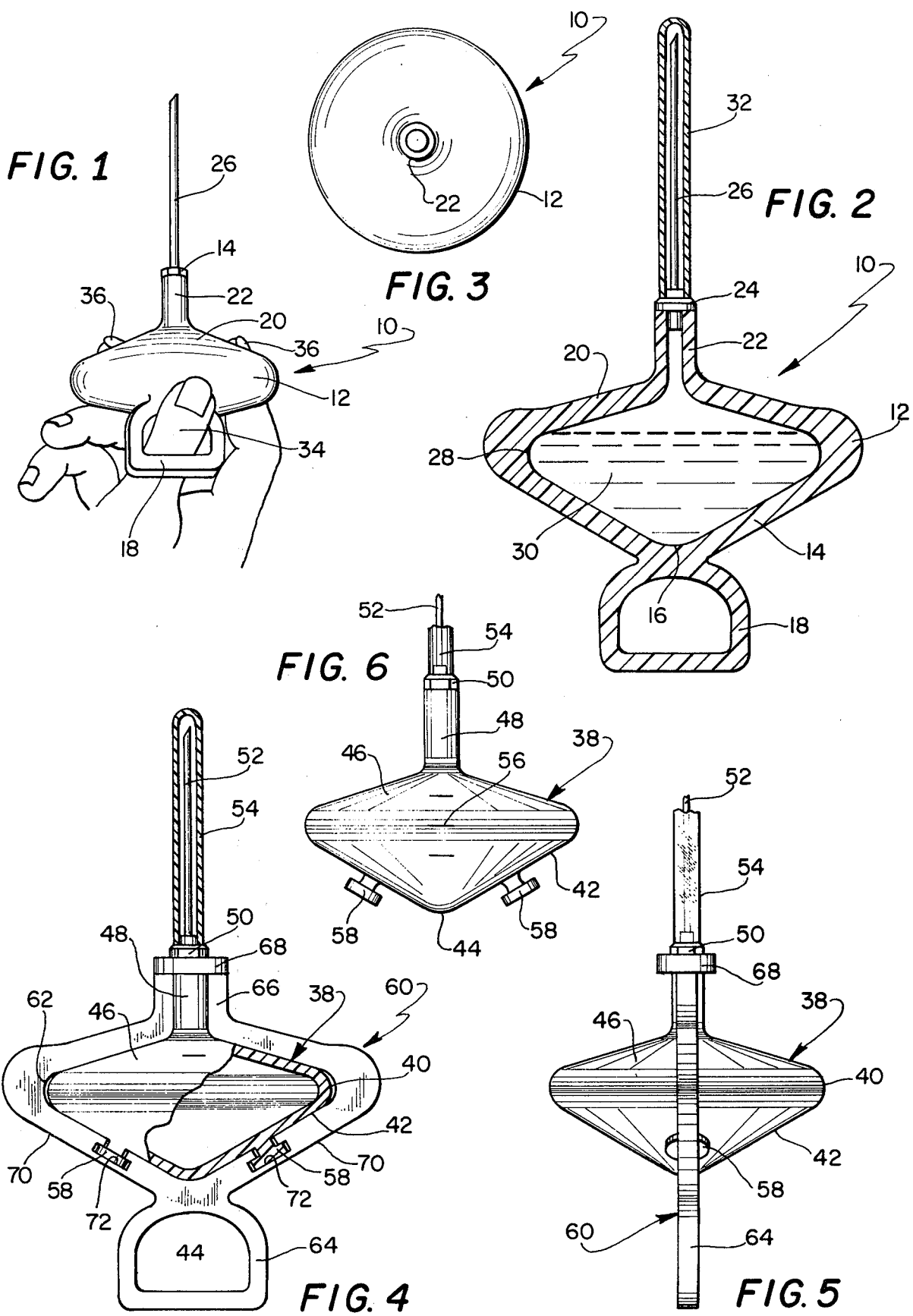

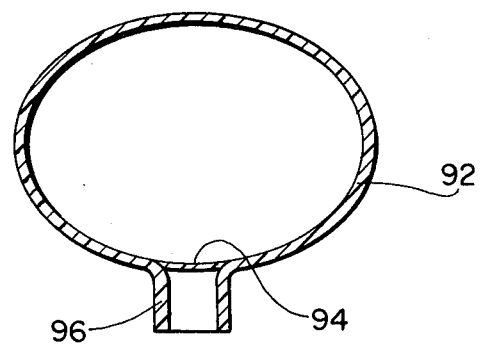
FIG. 10
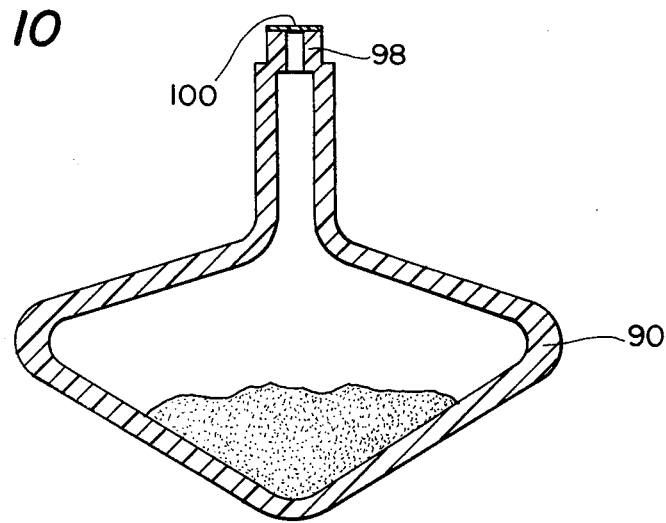
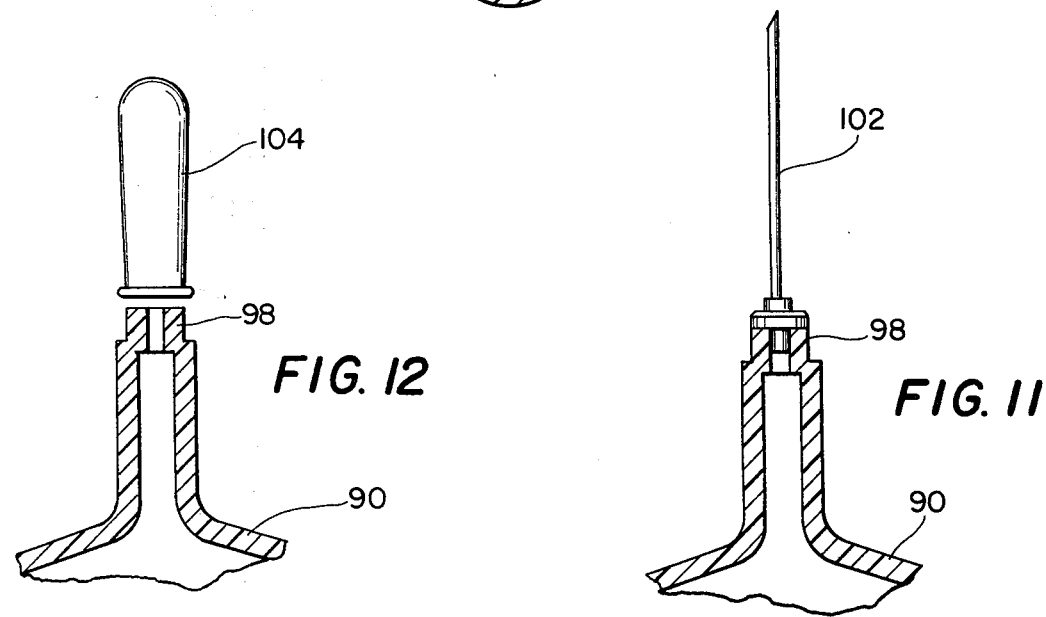
FIG. 12
FIG. 11

PREDOSED DISPOSABLE SYRINGE

BACKGROUND OF THE INVENTION

The present application is a continuation application of our Application Ser. No. 162,134 filed June 23, 1980, now abandoned, entitled PREDOSED DISPOSABLE SYRINGE which application is a continuation-in-part of our applications, Ser. No. 912,386 filed June 5, 1978, now abandoned, entitled PREDOSED DISPOSABLE SYRINGE and Ser. No. 931,209 filed Aug. 4, 1978, now abandoned also entitled PREDOSED DISPOSABLE SYRINGE.

Physicians, dentists, nurses and paramedics make numerous injections during the course of the day. These include various substances such as local anesthetics, insulin, sedatives, antihistamines, adrenalin, etc. Each injection must be accurately measured to ensure a proper dosage. In the conventional usage, a package of a presterilized needle must be opened and the needle mounted on a syringe which has been previously sterilized in the office. The medication is provided in a sterile bottle which must be opened and the needle pushed through a rubber or similar top. The syringe is now pumped to pick up the medication carefully to ensure the right dose. Only then is the injection ready to be given. The entire procedure is a slow and time consuming process. Another type of injectable delivery system is the administration of a local anesthetic using glass ampules with a separate syringe for delivery.

SUMMARY OF THE INVENTION

The present invention provides a predosed disposable syringe which eliminates all preparation and measurement. The device provides a single dose of medication in a predetermined quantity in a container which also acts as a syringe. The needle is already mounted on the container and the entire unit is provided in a sterile package. The physician merely opens the proper package and injects the medication. The unit is then thrown away, being entirely disposable. If desired, a separate holder may be provided in which the predosed unit container and needle may be placed for the injection. In such cases, the holder need not be sterile and can be used over again with other containers. The containers are shaped in the form of a double cone, tapering up and down from an annular central wide portion. The material is flexible so that the container can be readily compressed to eject the medication. At the top, a shot vertical neck is provided with means for mounting the hyperdermic needle. The needle may be premounted so that the entire unit is complete and ready for use. At the bottom, the container is provided with an integral loop for receiving the thumb. With the thumb through the loop and two forefingers over the top, the container is readily squeezed for injection or pulled open for aspiration. In another form, a separate holder is provided having a central opening for receiving the container. The thumb is now part of the holder, and the container is provided with male tabs adapted to enter slots in the holder. Pressure on the holder will compress the container to eject the dose of medication. Where the medication cannot be stored because it decomposes rapidly, or where there are many interchangeable components to vary the medication, the needle is replaced by a flexible pod which is separated from the container by a frangible membrane. A dry component of the medication is positioned in the container and the diluent is placed in the pod, or vice versa. Just prior to use, the pod is squeezed to break the membrane and force the component into the container. Manual agitation will help dissolve the powder, the container being transparent for visual inspection. The pod is removed and replaced by the needle. The device can readily be used for medication for infants, or animals, or people with oral problems by mounting a nipple or pliable extension on the container after the components have been mixed.

DESCRIPTION OF THE DRAWINGS

In the drawings:

FIG. 1 is a perspective view of a predosed disposable syringe embodying our present invention;

FIG. 2 is an enlarged vertical section thereof;

FIG. 3 is a top plan view thereof;

FIG. 4 is a side elevation, partly in section, of another form of our invention;

FIG. 5 is an edge view thereof;

FIG. 6 is a side elevation of the container for the form shown in FIG. 4;

FIG. 10 is an enlarged vertical section of another form of the invention;

FIG. 11 is a detail of the needle mounted on the form shown in FIG. 10; and

FIG. 12 is a view similar to FIG. 11 showing the mounting of a nipple in place of the needle.

DESCRIPTION OF THE INVENTION

Figure 7:
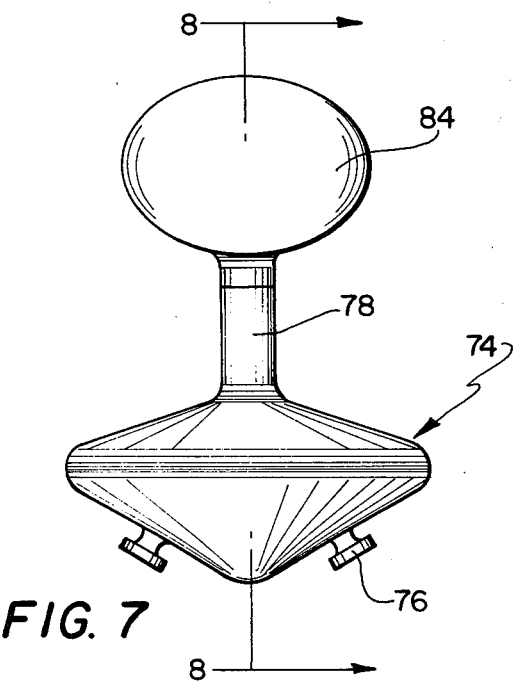
FIG. 7 is a side elevation of a container and pod for holding a rapidly decomposable solution.

Referring more in detail to the drawings, FIGS. 1, 2 and 3 illustrate a construction in which the container of a premeasured dose of a particular medication also acts as a syringe for injecting the dose. The container is pliable, flexible and readily manipulated. A thin rubber, polypropylene, polyethylene or elastomers may be used.

The body of the container 10 is annular and forms a double conical shape. From a wide central portion 12, the body tapers downwardly at 14 to a central point 16. At this point an integral loop member 18 depends downwardly, the loop opening being adapted to receive the thumb. At the upper end, the wall 20 tapers up at a flatter angle and terminates at the center with a short vertical neck 22. At the neck 22, means 24 are provided for holding the hyperdermic needle 26.

As can be seen in FIG. 2, the container 10 is provided with a thickened wall portion 28 at the inner part of the mid area 12 to eliminate sharp corners and ensure that the entire dose is expelled without a residue. It is also desirable to make the body 10 transparent so that the medication 30 is visible. This allows for visual monitoring of the dose. The needle 26 is illustrated with a conventional cover 32 which also serves to protect the sterility of the needle. However, it is contemplated that the entire unit be sterilized and sealed at the point of assembly.

In use, the physician, dentist, osteopath, nurse, or other qualified person, opens a sealed sterile package of the desired injection. Note that the container holds a premeasured dose. It is placed in the hand as shown in FIG. 1, with the thumb 34 through the loop 18, and the fingers 36 on the top 20. It is then easy to insert the needle and squeeze the body 10 to eject the dose through the needle. When the needle is first inserted, the thumb loop permits a short rearward pull to aspirate a drop of blood to check the position of the needle.

The entire unit is now disposable and has no further use. If desired, the unit of predosed medication may be provided without the needle. Since the needles are now supplied in sterile disposable form, the needle can be mounted at 24 prior to use. In any event, the use of the container 10, with its premeasured dose, eliminates much of the time consuming steps which now are taken with conventional syringes.

The form illustrated in FIGS. 1, 2 and 3 provides a container forming a one-piece syringe for the injection. In the form illustrated in FIGS. 4, 5 and 6, the container does not act as a syringe per se, but is placed in a complementary holder for forming the syringe.

Referring to FIG. 6, the container 38 is shaped similarly to the container 10. A central wide annular portion 40 tapers downwardly at 42 to a central point 44. At the top, the wall portion 46 tapers at a flat angle to an elongated integral vertical neck 48 on which the needle holder 50, needle 52 and cover 54 are mounted. In this form it is preferred that the container 38 be transparent and provided with calibration lines 56 to indicate ¼, ½ and ¾ doses.

The lower wall portion 42 is provided with a pair of male tab members 58, in alignment one on each side of the center 44. Each tab member 58 has a narrow neck and an enlarged head.

Viewing FIGS. 4 and 5, we now provide a holder 60 of a flat flexible material having a central opening 62 corresponding to the outer shape of the container 38. At the bottom, the holder 60 is provided with an integral thumb loop 64. At the top, the holder is provided with spaced upwardly extending portions 66 terminating in an integral annular loop 68.

The lower walls 70 of the opening 62 are provided on each side with female slots 72 with narrow necks and wide openings. As can be seen in FIG. 4, the container 38 is mounted in the holder 60 by passing the needle 52 upwardly through the loop 68 and positioning the container 38 in the opening 62, pressing tabs 58 into the slots 72. The entire unit now constitutes a syringe. Pressure on the holder 60 with thumb and fingers will collapse the container 38 and eject the desired dose through the needle 52. The thumb loop 64 permits a slight pull prior to injection to aspirate a drop of blood for checking the position of the needle.

In this form, the container 38 and needle are disposable. However, the holder 60 may be used over again and requires no sterilization. The calibration 56 and transparent container permit a visual inspection of what has been injected and how much is still left to inject. This is often desirable when injecting a local anesthetic.

Figure 8:
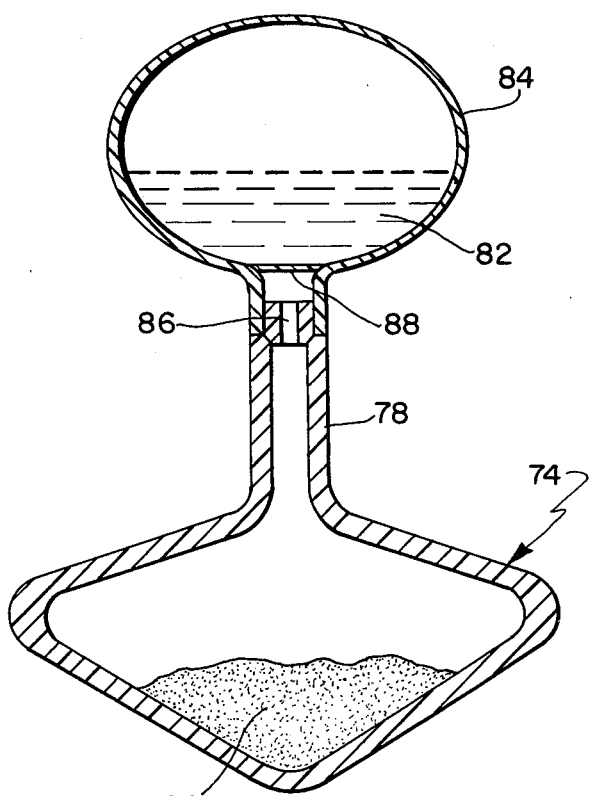
FIG. 8 is an enlarged section taken on line 8—8 on FIG. 7.

Some drugs will decompose relatively rapidly and thus cannot be stored in the container. In such cases, the form shown in FIGS. 7, 8 and 9 may be used. In this form, the container 74 is identical to the container 38, FIG. 6, with tabs 76 and an integral neck 78. However, in this form the container holds only one element, such as the dry powder 80, while its diluent 82 is housed in a pod 84 mounted on the neck 78 on the restricted neck portion 86. The pod 84 is provided with an integral thin membrane 88, FIG. 8, which seals the diluent in the pod and separates the pod from the container. The pod 84 should be of a thin flexible and transparent material and the container 74 should also be transparent.

Figure 9:
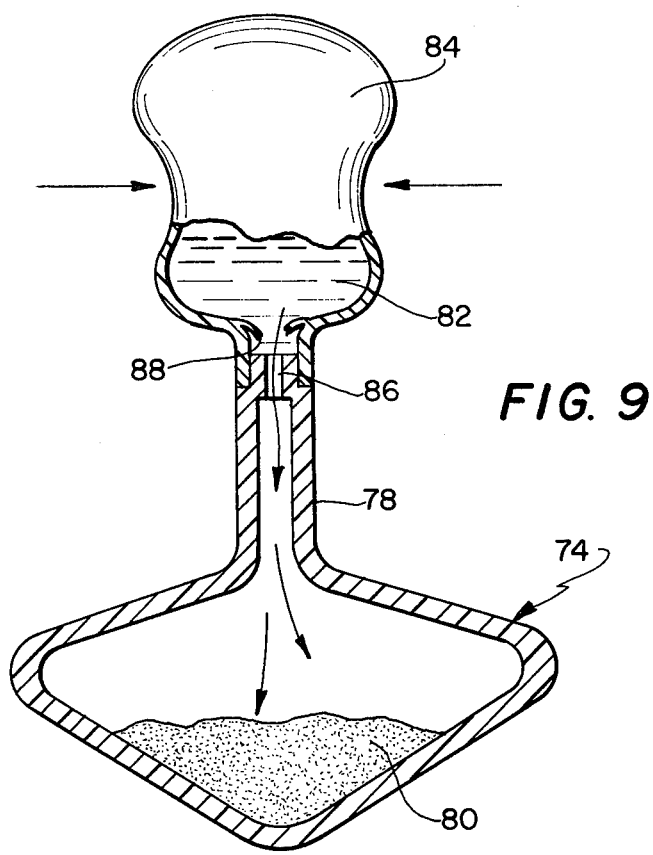
FIG. 9 is a view similar to FIG. 8 showing the mixing of the diluent with the dry medication to form a solution.

Just prior to administering the drug, the membrane 88 is broken by exerting a mechanical squeezing pressure on the pod 84, FIG. 9. This forces the diluent 82 into the container with the dry element 80. Mechanical agitation such as shaking dissolves the dry element in the diluent. The transparency of the container allows for visual inspection of the operation. Now the pod 84, emptied into the container, is removed and replaced by a sterile needle. The assembly is now identical to the container in FIG. 6 and is used in the same way.

The above construction lends itself to a great deal of versatility in the handling and storage of many variations in the formulas. Referring to FIGS. 10 and 11, the container 90 is preferably identical to the container 74 in the previous form, and the pod 92 is similar to the pod 84. However, in this form, the container may be provided with different diluent variations including combinations of chemicals, and the pod may be provided with different types of standard chemicals. The pod 92 is sealed with the thin membrane 94 and is provided with a neck 96 adapted to be easily fastened (as by a bayonet connection) to the neck 98 of the container 90. The container neck 98 may also be closed with the membrane 100.

With the above construction, several different types of diluent can be combined with several different types of dry chemicals to allow for a large variation of formulas with very small storage problems. If desired, the positions of the dry chemicals and the diluents can be reversed. The decision as to which combination of chemicals to use can be made by the physician or dentist on the spot and just prior to making the injection. After the pod 92 is locked to the neck 98, pressure on the pod will cause the membranes 94 and 100 to rupture and allow mixing. The pod 92 can now be removed and replaced by the needle 102, FIG. 11.

This concept lends itself to additional advantages. For example, viewing FIG. 12, a nipple 104 may be mounted on the portion 98 instead of the needle to allow for administering the dose orally. This is important in the case of small children or babies and in the case of animals. This system is also useful for psychiatric, geriatric, or adult patients with oral impairments.

The present invention thus provides a premeasured dose of a medication in a sterile container which also doubles as a syringe by itself or with a holder. Adrenalin, pain killers, local anesthesia, sedatives, antibiotics, serum, etc., are a few of the medicines which can be provided in premeasured doses. Since the unit is self-contained and sterilized at the point of assembly, the time consuming preparation for an injection is virtually eliminated. The proper medication and dosage is selected the sterile package is opened, and the injection is ready to be administered. The construction is fairly simple and economical. Where rapidly decomposing solutions must be used, the construction provides for the separation of the component elements until just prior to the injection.

Note that the needle is not needed to draw a dose from a container for mixing prior to injection and inserting into a second container. This virtually eliminates the possibility of contamination and loss of sterility of the needle. In cases where special formulations must be used, for example in a hospital, the container may be supplied empty and filled by the pharmacist. This takes the guesswork away from the nurse administering the dose, since the container is designed to hold a single measured dose only and is disposable. The construction shown in FIGS. 10, 11 and 12 has the additional advantage of keeping the inventories low. A common diluent can serve many combinations. Other advantages of the present invention will be readily apparent to a person skilled in the art.

What is claimed is:

1. A disposable syringe comprising a flexible compressible container for medication to be administered, means on said container for mounting a needle thereon, and means for compressing said container to eject the medication through said needle, said entire unit being sterilized, said compressing means comprising a holder for said container, means for mounting said container in said holder, said holder comprising a flat flexible member having a central opening for receiving said container therein, the bottom of said container being provided with outwardly extending tabs and said holder opening being provided with slots for receiving said tabs therein.

2. A disposable syringe comprising a flexible compressible container for medication to be administered, means on said container for mounting a needle thereon, and means for compressing said container to eject the medication through said needle, said entire unit being sterilized, said compressing means comprising a holder for said container, means for mounting said container in said holder, said holder comprising a flat flexible member having a central opening for receiving said container therein, said holder being formed with an integral loop at the bottom for receiving a thumb of the user therein, said holder being provided with a pair of spaced integral vertical members having a horizontally disposed loop at the top thereof, said needle extending through said loop when said container is mounted in said holder.

3. A syringe assembly, comprising a disposable container formed of a flexible and compressible material for receiving a predosed medicated fluid for the administration thereof, a separately formed holder, said container being removably mounted in said holder in interlocking engagement therewith, means formed on said holder for releasably interlocking said container in engagement therewith, said holder having a shape and configuration that provides for inwardly flexing movement thereof upon the application of external pressure thereto, said container having a neck portion formed thereon that extends upwardly from the top thereof, and fluid delivery means mountable on said neck portion, wherein upon the application of external pressure to said holder to effect a flexing movement thereof, said container is compressed with even pressure and said medicated fluid located therein is evenly injected through said fluid delivery means, a flexible pod being removably mountable on the neck portion of said container, a diluent contained in the pod or container and a dry powdered medicated material contained in the other, and a thin frangible membrane located in said pod and separating the interior of said pod from the interior of said container, wherein external pressure applied to said pod causes said membrane to fracture to allow the diluent to mix with said powdered medicated material to form a preselected medicated fluid for being received in said container, said pod thereafter being removable from said container to permit the mounting of said fluid delivery means on said neck portion for the dispensing of said medicated fluid therethrough, said holder comprising flat flexible member having a central opening adapted to receive said container, wherein the bottom of said container is provided with outwardly extending tabs and said holder opening is provided with slots adapted to receive said tabs.

4. A device as claimed in claim 3, wherein said container holds a single premeasured dose of the medication.

5. A syringe assembly comprising a disposable container formed of a flexible and compressible material for receiving a predosed medicated fluid for the administration thereof, a separately formed holder, said container being removably mounted in said holder in interlocking engagement therewith, means formed on said holder for releasably interlocking said container in engagement therewith, said holder having a shape and configuration that provides for inwardly flexing movement thereof upon the application of external pressure thereto, said container having a neck portion formed thereon that extends upwardly from the top thereof, and fluid delivery means mountable on said neck portion, wherein upon the application of external pressure to said holder to effect a flexing movement thereof, said container is compressed with even pressure and said medicated fluid located therein is evenly injected through said fluid delivery means, said interlocking means as formed on said holder being defined by slots, and lugs formed on said container corresponding in configuration to said slots for being received in interlocking engagement therewith.

6. A syringe assembly as claimed in claim 5, said holder including a thumb loop that is formed on the lowermost end thereof and that receives the thumb of the user for grasping the holder in the use of said assembly.

7. A syringe assembly comprising a disposable container formed of a flexible and compressible material for receiving a predosed medicated fluid for the administration thereof, a separately formed holder, said container being removably mounted in said holder in interlocking engagement therewith, means formed on said holder for releasably interlocking said container in engagement therewith, said holder being formed as a unitary construction of a flexible plastic material and with a central opening, said central opening receiving said container therein and providing for inwardly flexing movement of said holder upon the application of external pressure thereto for compressing said container, said container having a neck portion formed thereon that extends upwardly from the top thereof, and fluid delivery means mountable on said neck portion, wherein upon the application of external pressure to said holder to effect a flexing movement thereof, said container is compressed with even pressure and said medicated fluid located therein is evenly injected through said fluid delivery means.

8. A syringe assembly as claimed in claim 7, said container having a bulbous shape defined by a double cone configuration for receiving the predosed medicated fluid therein, said holder having outwardly inclined portions to which inwardly inclined portions are pivotally joined, said inwardly and outwardly inclined portions being relatively thin in cross-section and defining an opening therebetween, the configuration of which provides for receiving said bulbous container therebetween in relatively snug-fitting relation, wherein the flexing movement of said holder produces an even compressing action of said container.

9. A syringe assembly as claimed in claim 7, said predosed medicated fluid as received in said container being defined by a premixed diluent and medication of preselected measured amounts.

10. A syringe assembly as claimed in claim 9, said fluid delivery means being defined by an elongated needle of the hypodermic type.

11. A syringe assembly comprising a disposable container formed of a flexible and compressible material for receiving a predosed medicated fluid for the administration thereof, a separately formed holder, said container being removably mounted in said holder in interlocking engagement therewith, means formed on said holder for releasably interlocking said container in engagement therewith, said holder having a shape and configuration that provides for inwardly flexing movement thereof upon the application of external pressure thereto, said container having a neck portion formed thereon that extends upwardly from the top thereof, and fluid delivery means mountable on said neck portion, wherein upon the application of external pressure to said holder to effect a flexing movement thereof, said container is compressed with even pressure and said medicated fluid located therein is evenly injected through said fluid delivery means, a separately formed flexible pod removably mountable on the neck portion of said container, a diluent contained in either the pod or container and a dry powdered medicated material contained in the other, and a thin frangible membrane located in said pod and separating the interior of said pod from the interior of said container, wherein external pressure applied to said pod causes said pod to be contracted, wherein said membrane is fractured and the diluent thereafter mixes with said powdered medicated material in said container to form a preselected medicated fluid therein, said pod thereafter being removable from said container to permit the mounting of said fluid delivery means on said neck portion for the dispensing of said medicated fluid therethrough.

12. A syringe assembly as claimed in claim 11, said flexible pod having the powdered material disposed therein and said container having a diluent disposed therein prior to the mixing of the powdered material and diluent.

13. A syringe assembly as claimed in claim 11, said flexible pod having a diluent disposed therein and said container having the powdered material disposed therein prior to the mixing of the powdered material and diluent.

* * * * *